(12) United States Patent
Brazil (10) Patent No.: US 11,903,838 B2
(45) Date of Patent: Feb. 20, 2024

(54) REVISION KNEE SYSTEM (71) Applicant: SIGNATURE ORTHOPAEDICS EUROPE LTD, Dublin (IE)

(72) Inventor: Declan Brazil, Lane Cove West (AU)

( * ) Notice: Subject to any disclaimer, the term of this patent is extended or adjusted under 35 U.S.C. 154(b) by 197 days.

(21) Appl. No.: 17/291,364

(22) PCT Filed: Nov. 8, 2019

(86) PCT No.: PCT/AU2019/051227
§ 371 (c)(1),
(2) Date: May 5, 2021

(87) PCT Pub. No.: WO2020/093100
PCT Pub. Date: May 14, 2020

(65) Prior Publication Data
US 2022/0000627 A1    Jan. 6, 2022

(30) Foreign Application Priority Data
Nov. 9, 2018 (AU) .............................. 2018904290

(51) Int. Cl.
*A61F 2/38* (2006.01)
*A61B 17/88* (2006.01)
*A61F 2/30* (2006.01)

(52) U.S. Cl.
CPC .......... *A61F 2/389* (2013.01); *A61B 17/8802* (2013.01); *A61F 2/30734* (2013.01);
(Continued)

(58) Field of Classification Search
CPC ................. A61F 2/389; A61F 2/30734; A61F 2002/3069; A61F 2002/30736;
(Continued)

(56) References Cited

U.S. PATENT DOCUMENTS 5,290,313 A * 3/1994 Heldreth ................. A61F 2/389
623/20.15
5,509,934 A * 4/1996 Cohen ..................... A61F 2/389
623/20.32
(Continued)

OTHER PUBLICATIONS

International Preliminary Report on Patentability (Chapter II) dated Oct. 26, 2020 from PCT Application No. PCT/AU2019/051227.
(Continued)

*Primary Examiner* — Megan Y Wolf
(74) *Attorney, Agent, or Firm* — INNOVATION CAPITAL LAW GROUP, LLP; Vic Lin (57) ABSTRACT

A revision knee system has a unique polymeric tibial bearing monobloc defining both a superior condylar articular bearing surface and an inferior tibial bearing face. The inferior tibial bearing face bears directly on tibial cut surface so as to withstand compressive loading force applied to the superior condylar articular bearing surface thereof. The bearing component comprises a polymeric keel extending from the inferior bearing face which engages a higher strength metallic stem inferiorly with respect to the inferior bearing face and which may be configured to engage the stem in a structurally resilient manner despite the lower material strength of polymer as compared to metal.

19 Claims, 7 Drawing Sheets

(52) U.S. Cl.
CPC .............. *A61F 2002/3069* (2013.01); *A61F 2002/30166* (2013.01); *A61F 2002/30331* (2013.01); *A61F 2002/30433* (2013.01); *A61F 2002/30736* (2013.01); *A61F 2002/30878* (2013.01)

(58) Field of Classification Search
CPC .. A61F 2002/30878; A61F 2002/30779; A61F 2002/30777; A61F 2002/30607; A61F 2002/30604; A61F 2/3662; A61F 2002/30329; A61B 17/8802
See application file for complete search history.

(56) References Cited

U.S. PATENT DOCUMENTS

| | | | |
|---|---|---|---|
| 6,010,534 A | 1/2000 | O'Neil et al. | |
| 8,287,600 B2* | 10/2012 | Angibaud | A61F 2/389 623/20.15 |
| 9,468,531 B2* | 10/2016 | Cook | A61F 2/30 |
| 2005/0075735 A1 | 4/2005 | Berelsman et al. | |
| 2006/0195195 A1* | 8/2006 | Burstein | A61F 2/3868 623/20.33 |
| 2008/0091271 A1* | 4/2008 | Bonitati | A61F 2/38 623/20.32 |
| 2009/0082873 A1 | 3/2009 | Hazebrouck et al. | |
| 2010/0298947 A1 | 11/2010 | Unger | |
| 2012/0209391 A1* | 8/2012 | Cipolletti | A61F 2/389 623/18.11 |
| 2013/0024001 A1* | 1/2013 | Wentorf | A61F 2/4684 623/20.32 |
| 2014/0200674 A1* | 7/2014 | Mehta | A61F 2/389 623/20.34 |
| 2016/0022426 A1 | 1/2016 | Nevins | |

OTHER PUBLICATIONS

International Search Report & Written Opinion dated Mar. 4, 2020 from PCT Application No. PCT/AU2019/051227.

* cited by examiner

DETAIL C
SCALE 2:1

FIG. 10

DETAIL E
SCALE 2:1

REVISION KNEE SYSTEM

FIELD OF THE INVENTION

This invention relates generally to a revision knee systems.

BACKGROUND OF THE INVENTION

Revision knee surgery entails making of femoral and tibial chamfers and affixing respective bearing componentry thereto.

Tibial bearing componentry is anchored to the tibia epiphysis/medullary cavity with an inferior stem and forms a condylar articular surface for the femoral component.

Most tibial bearing componentry comprises a tibial tray to which a polymeric bearing is a fixed. One such typical arrangement comprising a tibial tray and removable polymeric bearing is disclosed in US 2009/0082873 A1 (HAZEBROUCK et al.) 26 Mar. 2009 [hereinafter referred toc as D1] which discloses a fixed-bearing knee prosthesis which has a polymeric bearing secured to a tibial tray. The tibial tray of D1 has a metallic platform which lies on a tibial cut surface and which has an inferior anchoring stem.

US 2008/0091271 A1 (BONITATI et al.) 17 Apr. 2008 [hereinafter referred to as D2] discloses a similar metallic tray arrangement but wherein the metallic tibial tray comprises a bore and a stem of the polymeric bearing inserts into the bore. The bearing by comprises tabs which non-rotatably engage slots within the tibial tray.

US 2005/0075735 A1 (BERELSMAN et al.) 7 Apr. 2005 [hereinafter referred to as D3] discloses a prosthesis rather for the elbow but which comprises a radial head component which may be slid onto a mounting portion of an anchoring portion for adjusting the height and angle of a radial head.

Some systems may employ a metallic stem that is removeable from the tibial tray, as those of the Stryker™ Triathlon™ or Biomet™ Vanguard™ 360 revision knee systems.

The present invention seeks to provide a revision knee system which is less costly manufacture whilst yet being mechanically resilient, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein a revision knee system comprising a polymeric tibial bearing monobloc (such as of high molecular weight polyethylene, ultra-high molecular weight polyethylene (UHMWPE), polyether ether ketone (PEEK) or the like) defining a superior condylar articular bearing surface for a femoral component. The tibial bearing monobloc also defines a planar inferior bearing face.

The tibial bearing monobloc further comprises a keel extending inferiorly from the inferior bearing face. The tibial bearing monobloc including keel may be integrally manufactured from machine or compressive moulding as a single unit.

The present system further comprises an inferior stem comprising an insertion end and a superior keel engaging end.

The keel, extending inferiorly from the polymeric inferior tibial bearing face, is configured to engage the keel engaging end at an inferior position with respect to the inferior tibial bearing face As such, in use, for knee revision surgery which prepares a tibial cut surface of a tibia, the keel engaging end of the stem can be engaged to the keel at the inferior position.

The inferior stem can then be inserted through a tibial cut surface of the tibia such that the inferior tibial bearing face of the tibial bearing monobloc bears flush against the tibial cut surface so as to withstand compressive loading force applied to the superior condylar articular bearing surface thereof by the femoral component and the keel engages the keel engaging end beneath the tibial cut surface.

As such, the present system allows for the low-cost manufacture of knee prosthesis componentry without expensive manufacturing processes for metallic tibial tray componentry.

Specifically, the integrally formed tibial bearing monobloc of low-cost polymeric material such as high molecular weight polyethylene or the like defines both the superior condylar articular bearing surface and the polymeric inferior tibial bearing face, hitherto usually being formed by an undersurface of a platform of tibial trays such as of prior art devices such as D1-D3.

Unlike prior art arrangements wherein a tibial tray bears on the tibial cut surface and supports a polymeric bearing on a platform thereof, the tibial bearing face of the polymeric tibial bearing monobloc itself bears upon the tibial cut surface to withstand compressive loading force applied to the superior articular bearing surface of the polymeric tibial bearing monobloc.

Furthermore, unlike prior art arrangements, the present keel engages the keel engaging end at an inferior position with respect to the inferior tibial bearing face. Preferably, the stem does not extend substantially above the tibial bearing face or no part of the stem extends above the tibial bearing face, thereby not compromising the structural integrity of the tibial bearing monobloc above the inferior tibial bearing face, allowing for minimisation of the thickness thereof.

The keel may extend outwardly from the keel engaging end in a transverse plane such that, in use, the keel engages spongy bone beneath the tibial cut surface. The keel may be non-circular in the transverse plane so as to non-rotatably engage spongy bone beneath the tibial cut surface in use. The keel may comprise at least one span which extends outwardly from the engaging end in the transverse plane, the at least one span defining at least one edge which engages the spongy bone.

The keel may occupy less than 60% cross section across the tibial bearing face, and preferably even less, to maximise the available surface area of the tibial bearing face.

The keel may be designed to increase the structural rigidity thereof despite allowing for sufficient inferior tibial bearing face surface area and the lower material strength of polymeric as compared to metal. As such, the keel may widen towards the tibial bearing face, including to a cross-section greater than a maximum cross-section of the keel engaging end of the stem.

The keel may comprise adjacent spans which tightly fit the keel engaging end therebetween. The keel may further comprise a vertical joining member between the adjacent spans and the keel engaging end may be forked so as to engage either side of the vertical joining member and be engaged between inner surfaces of the adjacent spans.

The spans may extend mediolaterally for enhancing mediolateral structural integrity. Furthermore, the engaging end may comprise a backstop tine defining an anteriorly orientated surface which bears against a posteriorly orientated surface of a lower edge of the keel for enhancing anteroposterior structural integrity.

The system may further comprise spacer augments for filling gaps of removed diseased or unstable bone.

The spacer augments may define open mediolaterally orientated channels therethrough for accommodating respective edges of spans of the keel therein and which may be provided in left and right-handed configuration so as to connect under the tibial bearing medially or laterally.

The spacer augments may be conformingly shaped for stacking. The spacer augments may define connectors for connecting to the inferior tibial bearing face or a superior augment. The connectors may comprise clips or raised formations which interfere with corresponding inner edges of cavities within the tibial bearing face.

The augments may comprise a plurality of bone cement passages which allow bone cement to flow therethrough including while stacked. The polymeric tibial bearing monobloc may have inferior cavities corresponding in location to the passages such that bone cement can penetrate the polymeric tibial bearing monobloc, including via the bone cement passages.

According to one aspect, there is provided a revision knee system comprising: a polymeric tibial bearing monobloc defining a superior condylar articular bearing surface for a femoral component and a planar inferior tibial bearing face, the tibial bearing monobloc having a keel extending inferiorly from the inferior tibial bearing face; an inferior stem comprising an insertion end and a superior keel engaging end, wherein: the keel, extending inferiorly from the inferior tibial bearing face, is configured to engage the keel engaging end inferiorly with respect to the inferior tibial bearing face, such that, in use, for knee revision surgery which prepares a tibial cut surface of a tibia: the keel engaging end of the stem can be engaged to the keel inferiorly with respect to the inferior tibial bearing face, the inferior stem can be inserted through a tibial cut surface of the tibia such that: the inferior tibial bearing face of the tibial bearing monobloc bears flush against the tibial cut surface so as to withstand compressive loading force applied to the superior condylar articular bearing surface thereof by the femoral component; and the keel extends into the tibial cut surface and engages the keel engaging end of the stem beneath the tibial cut surface inferiorly with respect to the tibial bearing face.

The tibial bearing monobloc including keel may be integrally cast as a single unit during manufacture.

The stem may be metallic.

The keel may occupy less than 60% cross section across the tibial bearing face.

In embodiments, no part of the stem extends above the tibial bearing face.

The keel may extend outwardly from the keel engaging end in a transverse plane such that, in use, the keel engages spongy bone beneath the tibial cut surface.

The keel may be non-circular in cross-section in the transverse plane so as to non-rotatably engage the spongy bone beneath the tibial cut surface in use.

The keel may comprise at least one span which extends outwardly from the engaging end in a transverse plane, the at least one span defining at least one edge.

The at least one span may widens towards the tibial bearing face.

The at least one span may widens towards the tibial bearing face to a cross-section greater than a maximum cross-section of the keel engaging end of the stem.

The at least one span may comprise two adjacent spans which tightly fit the keel engaging end between respective inner surfaces thereof.

The two adjacent spans may extend mediolaterally.

The keel further may comprise a vertical joining member between the two adjacent spans, the engaging end may have two tines and the vertical joining member fits between the two tines.

The revision knee may further comprise fasteners which insert through apertures of the tines and through the vertical joining member.

The engaging end may comprise a backstop tine defining a backstop bearing face configured to bear against a lower edge of the keel.

The backstop bearing face may be anteriorly orientated.

The revision knee may further comprise a plurality of augments of differing thicknesses, each configured to engage the inferior tibial bearing face and wherein the augments are conformingly shaped to stack together.

Each augment may comprise a superior face comprising at least one connector configured for connecting to the inferior tibial bearing face.

Each augment may comprise an inferior augment bearing face defining an engagement for the at least one connector so as to be able to connect to an adjacent augment in use.

Each augment may comprise at least one bone cement passage between inferior and superior surfaces thereof.

The at least one passage may comprise a plurality of passages which are spaced around each augment.

The passages may correspond in location with corresponding cavities in the inferior tibial bearing face such that, in use, bone cement can penetrate into the polymeric tibial bearing monobloc via the at least one augment.

According to another aspect, there is provided a revision knee technique using the revision knee system the technique comprising preparing a tibia by preparing at least a tibial cut surface in a transverse plane, selecting the polymeric tibial bearing monobloc by size and connecting the keel thereof with the keel engaging end of the inferior stem inferiorly with respect to the inferior tibial bearing face, inserting the inferior stem into the tibial cut surface until the keel penetrates beneath the tibial cut surface to engage into spongy bone thereunderneath and the inferior polymeric tibial bearing face of the tibial bearing monobloc bears flush against the tibial cut surface so as to withstand compressive loading force applied to the superior condylar articular bearing surface thereof.

The technique may comprise removing unsuitable bone and selecting at least two augments having a height corresponding to a depth of the removed unsuitable bone, stacking the augments together and connecting the augments to the tibial bearing face of the tibial bearing monobloc.

The technique may further comprise applying bone cement which flows via collocating bone passages of the augments into cavities within the polymeric tibial bearing monobloc.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which.

DESCRIPTION OF EMBODIMENTS

A revision knee system 100 comprises a polymeric tibial bearing monobloc 101. The polymeric tibial bearing monobloc 101 is made of a polymer such as polyethylene, including heigh weight molecular weight polyethylene, ultra-high molecular weight polyethylene (UHMWPE), polyether ether ketone (PEEK) or the like.

The polymeric tibial bearing monobloc 101 defines a superior articular bearing surface 102 for a femoral component (not shown). The articular bearing surface 102 may be congruent with condylar bearing surfaces of the femoral component and may comprise a tibial post 103.

The tibial bearing monobloc 101 further defines an inferior tibial bearing face 104. The tibial bearing face 104 is preferably planar and aligned in the transverse plane.

The tibial bearing monobloc 101 further comprises a polymeric keel 105 extending inferiorly from the bearing face 104. The tibial bearing monobloc 101 and the polymeric keel 105 thereof may be integrally formed as a single unit from a machine or compression moulding process. However, in less preferred alternative embodiments the keel 105 may be snapped into or screwed into place.

The system 101 further comprises an inferior stem 106 comprising an inferior insertion and 107 and a keel engaging end 108. The stem 106 is preferably metallic.

The keel engaging end 108 and the keel 105 are configured engage together at an inferior position with respect to the inferior tibial bearing face 104. The inferior stem 106 may comprise longitudinal anti-rotation grooves 109.

As such, for knee revision surgery which prepares a tibial cut surface of a tibia, the keel engaging end 108 of the stem 106 can be engaged to the keel 105 at the inferior position, the inferior position being inferior with respect to the tibial bearing face 104.

The inferior stem 106 can then be inserted through a tibial cut surface of the tibia such that the inferior tibial bearing face 104 of the tibial bearing monobloc 101 bears flush against the tibial cut surface so as to withstand compressive loading force applied to the superior condylar articular bearing surface thereof by the femoral component; and the keel 106 engages the keel engaging end beneath the tibial cut surface.

The tibial bearing face 104 is configured for bearing the compressive loading forces of the knee and therefore may comprise sufficient surface area spread across the tibial cut surface. In embodiments, the keel occupies less than 60% cross section across the tibial bearing face, and preferably even less.

Preferably, no part of the stem 106 extends substantially or at all above the tibial bearing face 104 so as to avoid compromising the structural integrity of the monobloc 101 above the tibial bearing face 104. Furthermore, as shown, the keel 105 may extend outwardly from the keel engaging end 108 in a transverse plane such that, in use, the keel 105 engages spongy bone beneath the tibial cut surface. Furthermore, the keel 105 is preferably non-circular in cross-section and the transverse plane so as to non-rotatably engage the spongy bone.

The keel 105 may comprise at least one span 114 which extends outwardly from the engaging end 108 in the transverse plane. The at least one span 114 may define at least one edge 138. In the embodiments shown, the at least one span 114 extends either side of the engaging end so as to thereby defining opposite edges 138.

In a preferred embodiment shown, the keel 105 comprises two spans 114A and 114P. Preferably, these spans 114A and 114P tightly fit the engaging end 108 of the stem 106 therebetween. Specifically, the spans 114 may define inner anteroposterior bearing faces 115 therebetween and the engaging end 108 may define respective outer anteroposterior bearing faces 116 that bear tightly between the outer anteroposterior bearing faces 115.

The keel 105 may further comprise a vertical joining member 117 between the two spans 114A, 114P and the keel engaging end 108 may be forked, thereby defining two tines 110 and a channel 111 therebetween. The channel 111 may accommodate the vertical joining member 117. Fasteners 112 may locate through apertures 113 of the tines 111 so as to engage the vertical joining member 117 within the channel 111.

Preferably, the two spans 114A and 114P span mediolaterally.

The two spans 114A and 114P may define a channel 123 of uniform width therebetween into which the respective tines 110 may be inserted along a vertical axis.

The anteroposterior bearing faces 116 of the tines 110 may comprise directional teeth 124 thereon which bite into the channels 123.

The engaging end 108 may further comprise a backstop tine 118 comprising an anteriorly orientated bearing face 119 that bear oppositely against a corresponding posteriorly orientated bearing face 120 of a lower edge 121 of the keel 105. The backstop tine 118 may fork posteriorly to form a notch 122 within which the lower edge 121 of the posterior span 114P inserts.

The system 100 may further comprise spacer augments 125 which may engage regions of the inferior bearing face 104 of the tibial bearing monobloc 101.

Each spacer augments 125 may comprise a superior surface 126 which engages the inferior bearing face 104 of the tibial bearing monobloc 101 and an inferior augment bearing face 127.

Each augment 125 may comprise side open mediolaterally orientated channels 127 to accommodate respective edges 138 of the spans 114 such that the augment 125 may engage the keel 105 medially or laterally. In this regard, the augments 125 may be provided in left-handed and right-handed configurations for medial or lateral engagement to the keel 105.

The augments 125 may be conformingly shaped to allows stacking together and may be provided in differing thicknesses so as to fill gaps of various heights. For example, the augments 125 may be provided in 5 and 10 mm thicknesses for stacking together.

Superior surfaces 126 of the augments 125 may define connectors for connecting to the inferior tibial bearing face 104 or a superior augment 125.

The connectors may comprise clips 128 which clip against corresponding edges 129 formed within cavities 130 within the tibial bearing face 104.

Each augment 125 may similarly comprise edges 129 within cavities within the inferior augments bearing face 127 which may engage the clips 128 of an augment 125 thereunderneath.

Figure 1:
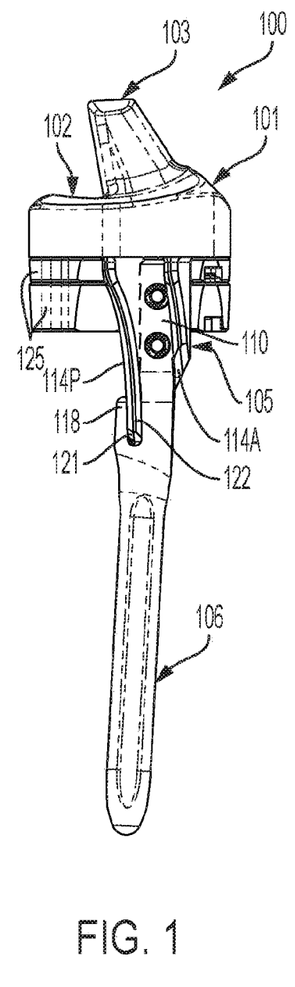
FIG. 1 shows a side elevation view of a revision knee system in accordance with an embodiment.
Figure 2:
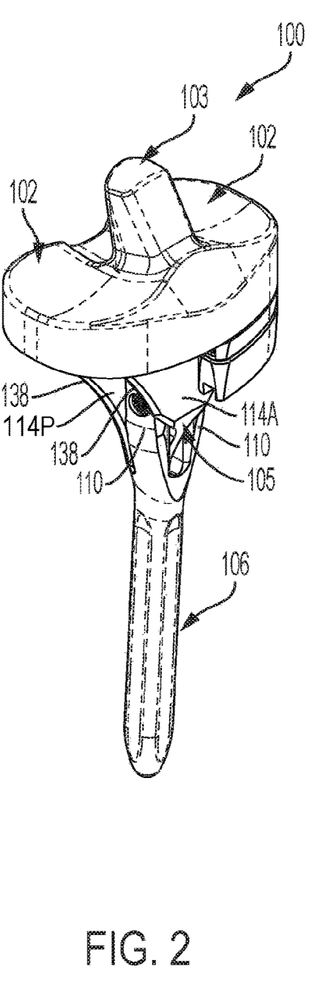
FIG. 2 shows a top perspective view of the revision knee system.
Figure 3:
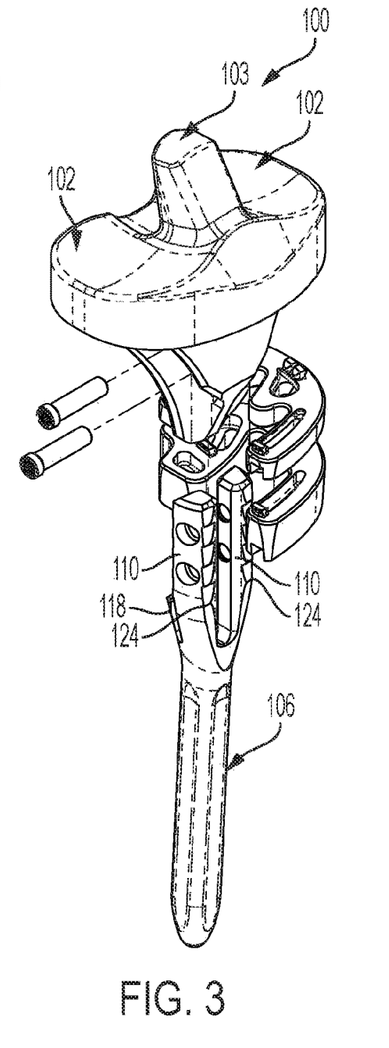
FIG. 3 shows a top perspective view of the revision knee system when disassembled.
Figure 4:
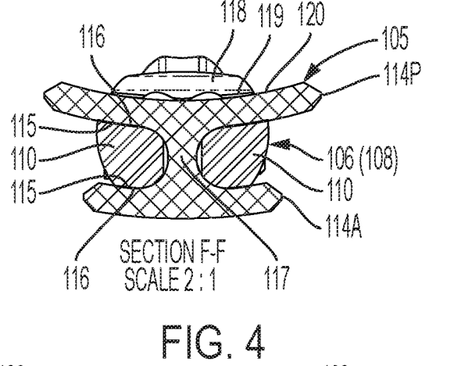
FIG. 4 shows a cross-sectional view of the revision knee system.
Figure 5:
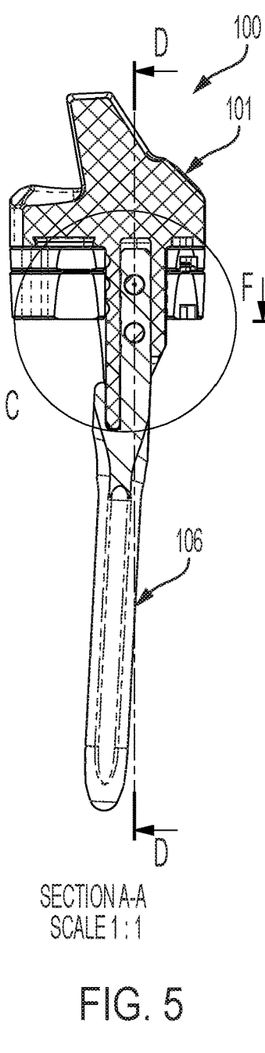
FIG. 5 shows a cross-sectional view of the revision knee system in a median plane.
Figure 6:
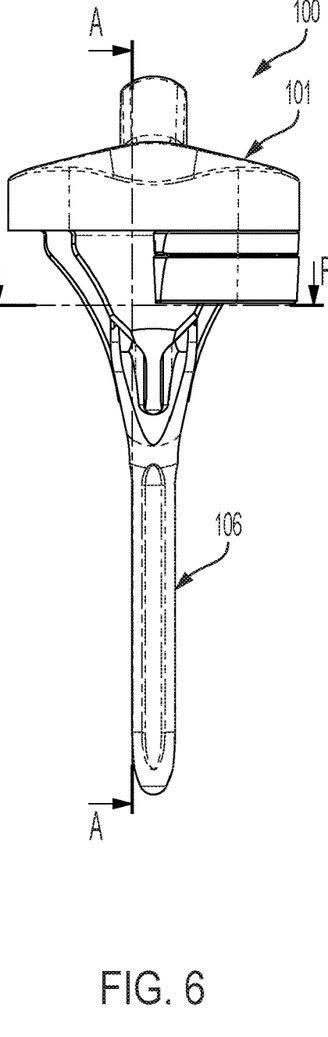
FIG. 6 shows an anterior elevation view of the revision knee system.
Figure 7:
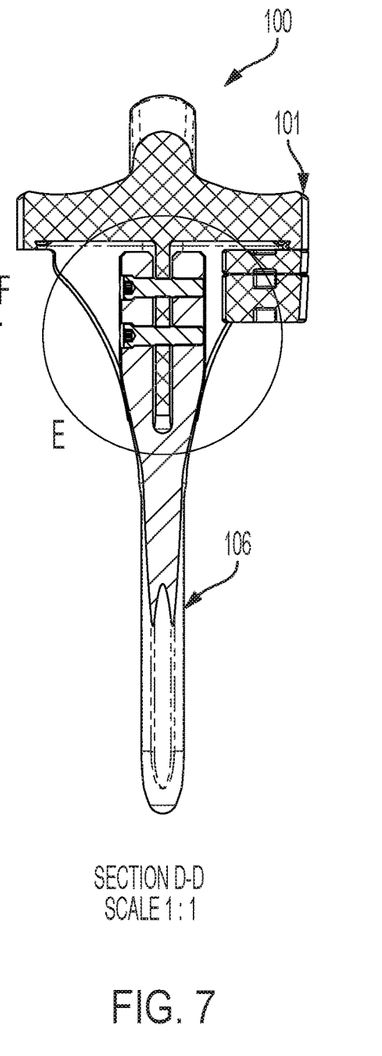
FIG. 7 shows a cross-sectional view of the revision knee system in a frontal plane.
Figure 8:
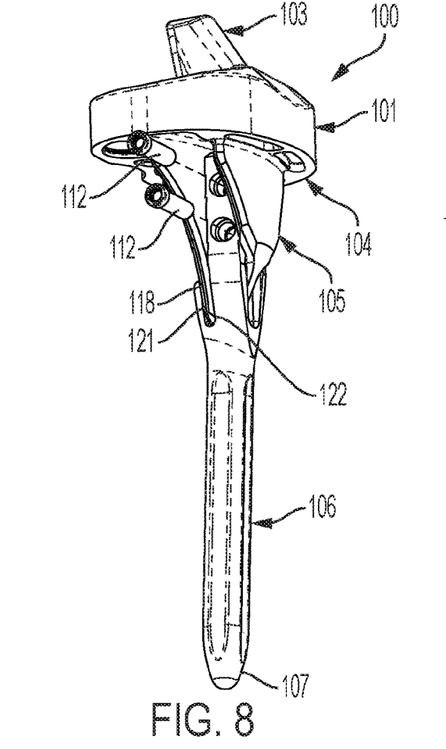
FIG. 8 shows a bottom perspective view of the revision knee system.
Figure 9:
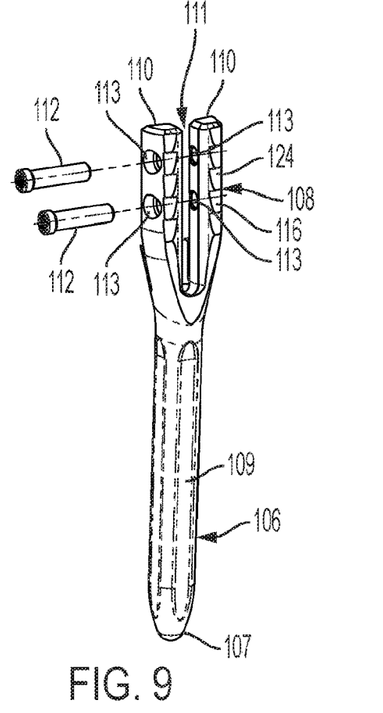
FIG. 9 shows a front perspective view of a stem of the revision knee system.
Figure 10:
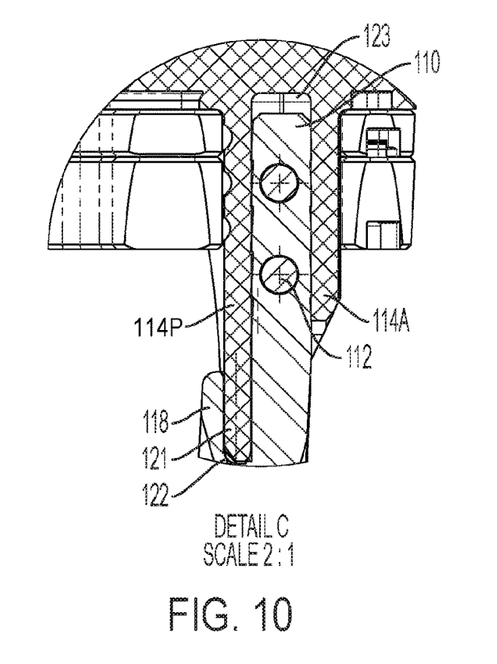
FIG. 10 shows a cross-sectional magnified view of the revision knee system in a median plane.
Figure 11:
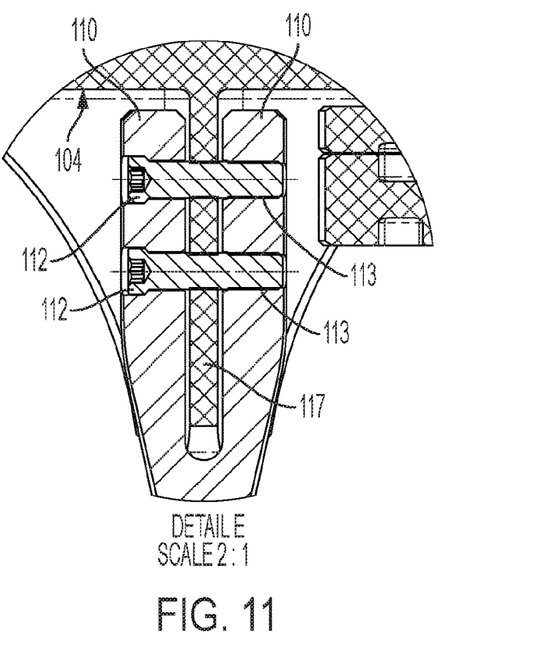
FIG. 11 shows a magnified cross-sectional view of the revision knee system in a frontal plane.
Figure 12:
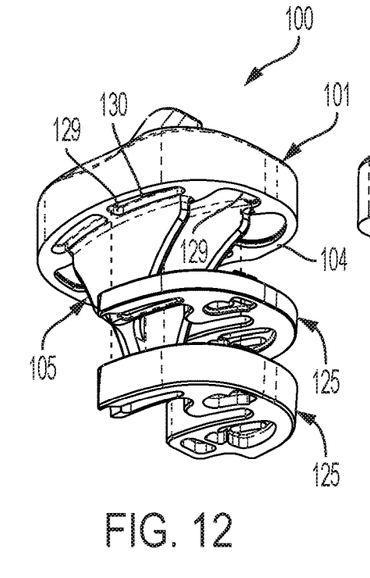
FIG. 12 shows a bottom perspective view of augments engaging a polymeric tibial bearing monobloc of the system in accordance with an embodiment.
Figures 13, 14:
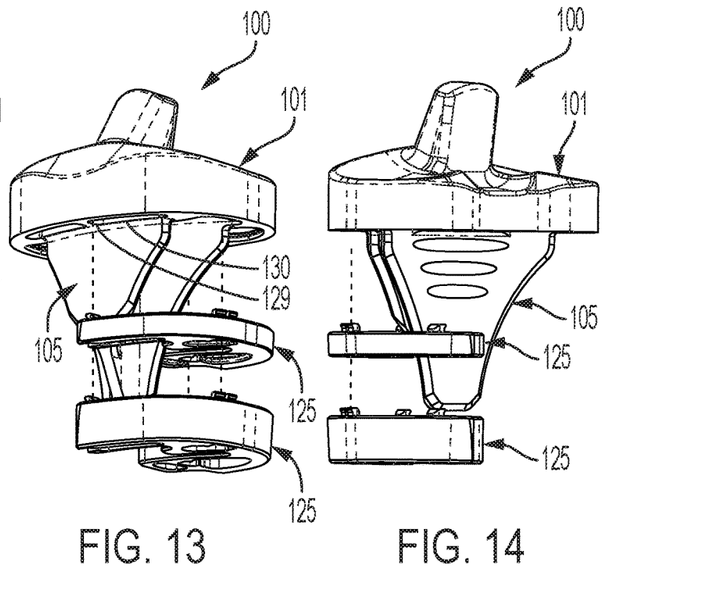
FIG. 13 shows a further bottom perspective view of the augments engaging the monobloc.
FIG. 14 shows a rear perspective view of the augments engaging the monobloc.
Figures 15, 16:
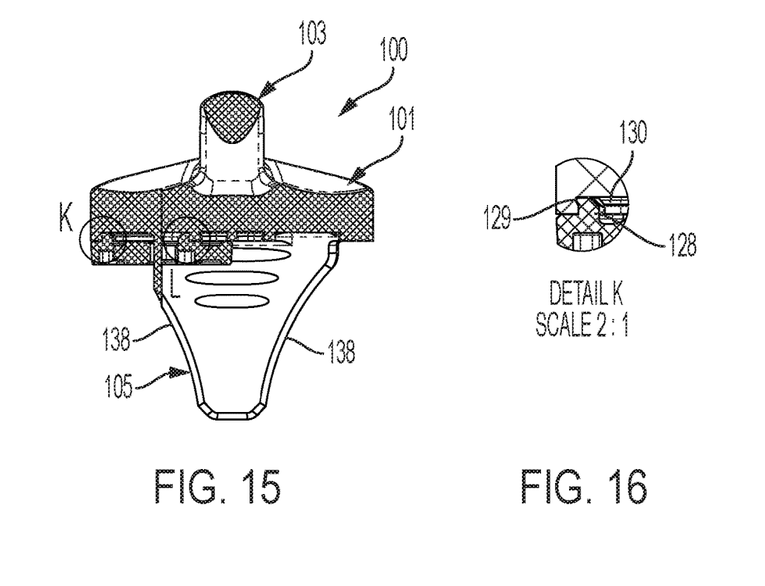
FIG. 15 shows a cross-sectional view in the frontal plane showing the augments engaging the monobloc.
FIGS. 16 and 17 show magnified views of connectors of an augments engaging the monobloc.
Figure 17:
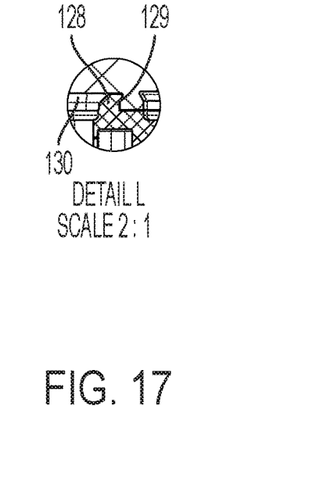
Figure 18:
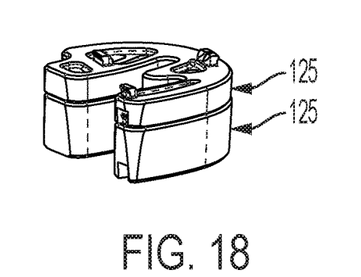
FIGS. 18-20 illustrate stacking together of augments in accordance with an embodiment.
Figure 19:
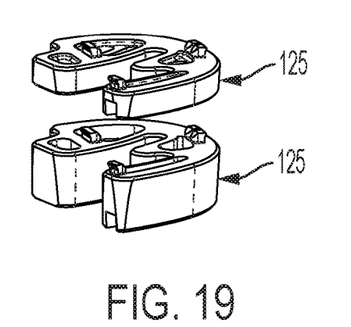
Figure 20:
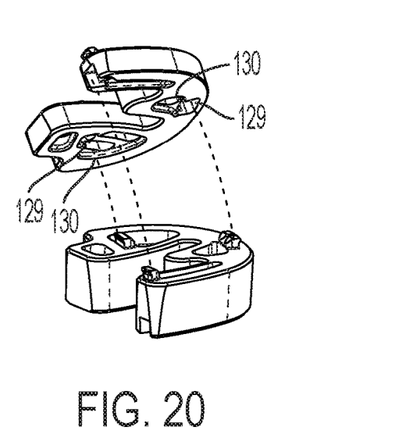
Figure 21:
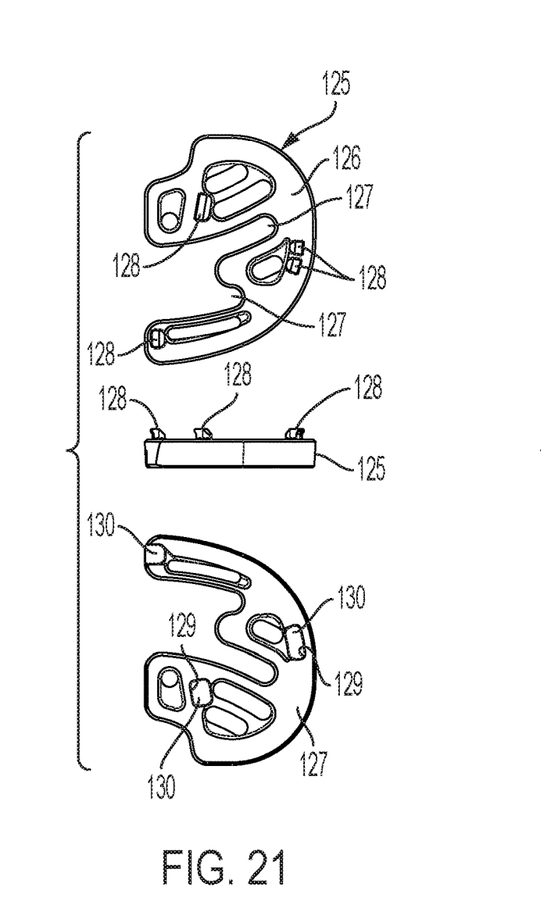
FIGS. 21 and 22 show top, side and bottom views of augments of two types of thicknesses in accordance with an embodiment.
Figure 22:
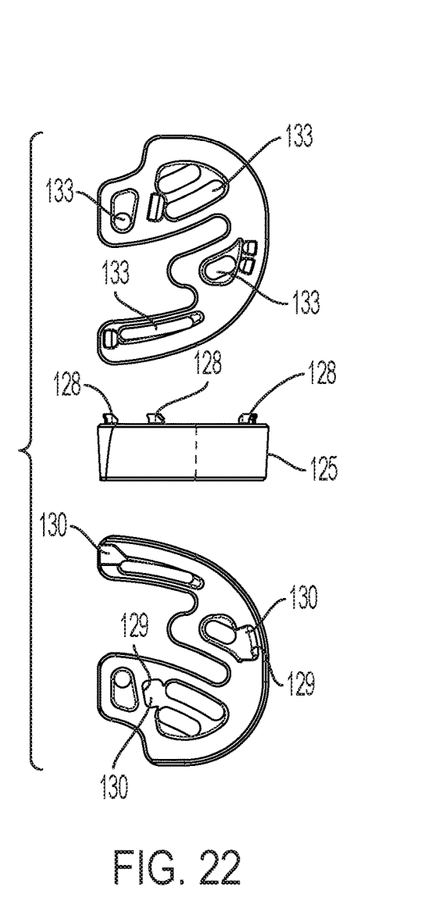
Figure 23:
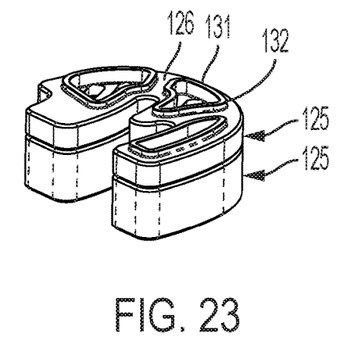
FIG. 23-25 shows stacking together of augments in accordance with a further embodiment.
Figure 24:
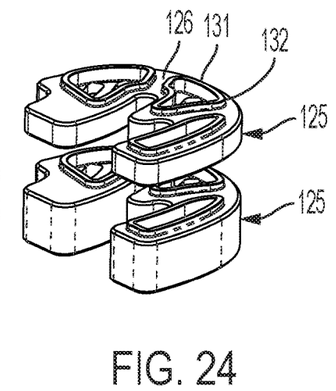
Figure 25:
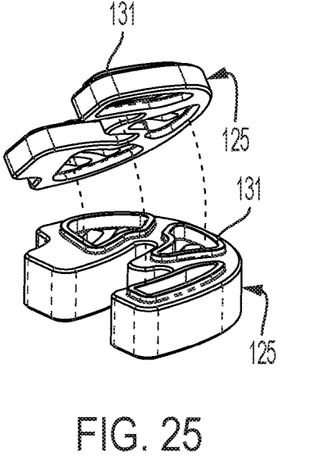
Figure 26:
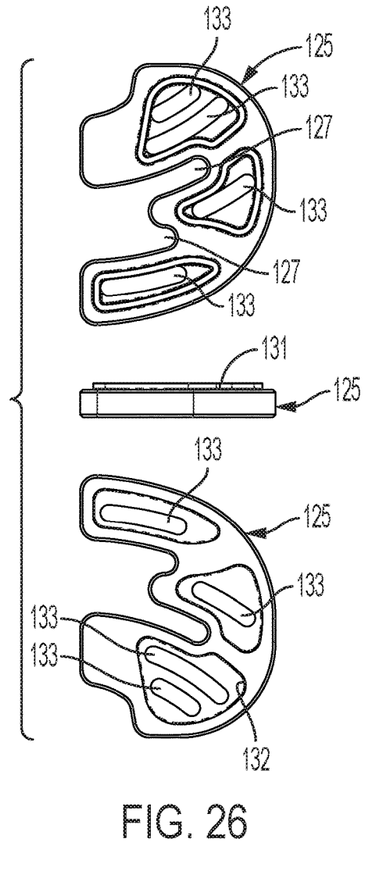
FIG. 26-27 shows a top, side and bottom views of augments of two types of thicknesses in accordance with a further embodiment.
Figure 27:
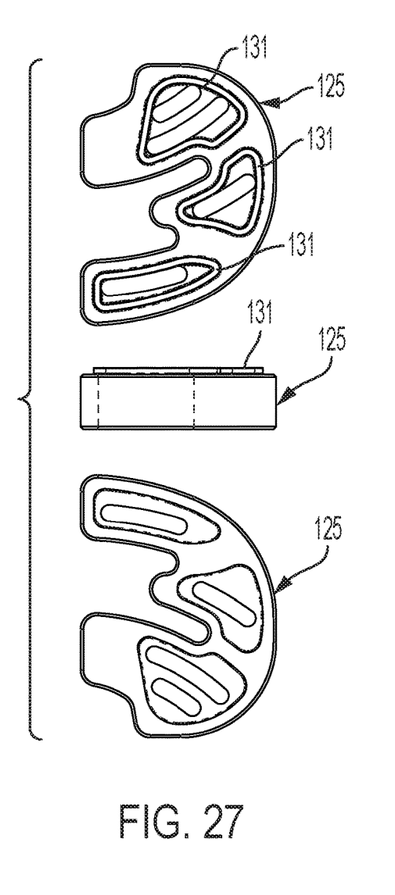
Figure 28:
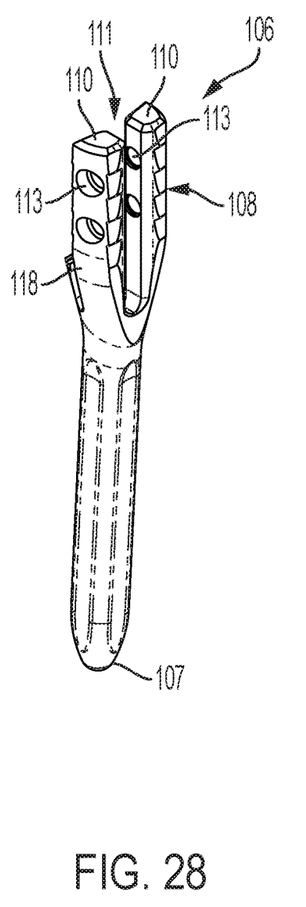
FIG. 28 shows a top perspective view of the stem.
Figure 29:
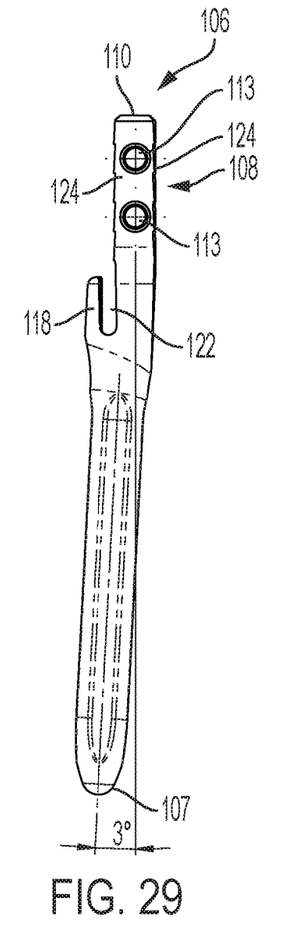
FIG. 29 shows a side elevation view of the stem.
Figure 30:
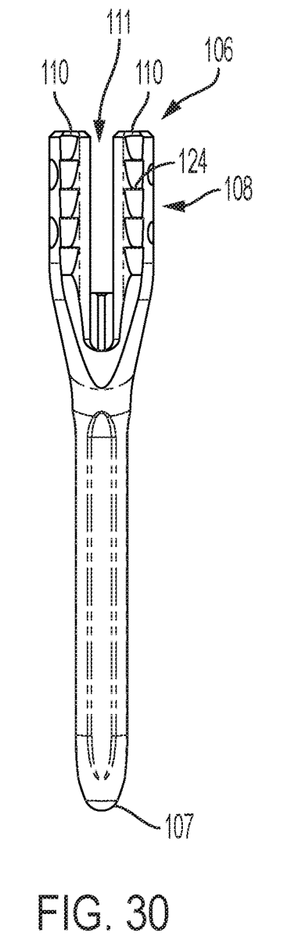
FIG. 30 shows an anterior elevation view of the stem.

As opposed to using clips 128, as shown in FIGS. 23-27, the superior surface 126 may comprise raised formations 131 defining an exterior edge 132 which engages a corresponding inner edge 132 of a cavity 130 an inferior augments bearing face 125 or a superior adjacent augment 125 or of the tibial bearing face 104.

The augments 125 may define bone cement passages 133 between the inferior augment bearing face 127 and superior surface 126 for flow of bone cement therethrough.

Preferably the bone cement passages 133 correspond with respective cavities 130 within the tibial bearing face 104 such that bone cement can flow into the polymeric tibial bearing monobloc 104, including via the augments 125.

The bone cement passages 133 may be spaced around each augment 125 to allow for flow of bone cement and various regions of the augment 125. The passages 133 of the augments 125 may collocate when the augments 125 when stacked, thereby forming a continuous passage through stacked augments.

The foregoing description, for purposes of explanation, used specific nomenclature to provide a thorough understanding of the invention. However, it will be apparent to one skilled in the art that specific details are not required in order to practise the invention. Thus, the foregoing descriptions of specific embodiments of the invention are presented for purposes of illustration and description. They are not intended to be exhaustive or to limit the invention to the precise forms disclosed as obviously many modifications and variations are possible in view of the above teachings. The embodiments were chosen and described in order to best explain the principles of the invention and its practical applications, thereby enabling others skilled in the art to best utilize the invention and various embodiments with various modifications as are suited to the particular use contemplated. It is intended that the following claims and their equivalents define the scope of the invention.

The term "approximately" or similar as used herein should be construed as being within 10% of the value stated unless otherwise indicated.

The invention claimed is:

1. A revision knee system comprising:
a polymeric tibial bearing monobloc defining a superior condylar articular bearing surface for a femoral component and a planar inferior tibial bearing face opposite the superior condylar articular bearing surface, the tibial bearing monobloc having a keel extending inferiorly from the inferior tibial bearing face; and
an inferior stem comprising an insertion end and a superior keel engaging end, wherein
the superior keel engaging end engages the keel inferiorly with respect to the inferior tibial bearing face along most of the length of the keel,
a portion of the keel forms an exterior of the revision knee system,
the keel extends outwardly from along the superior keel engaging end,
the keel comprises at least one span which extends outwardly from the superior keel engaging end in a transverse plane, the at least one span defining at least one edge,
the at least one span comprises two adjacent spans which tightly fit the superior keel engaging end between respective inner surfaces thereof, and
the keel further comprises a vertical joining member between the two adjacent spans, the superior keel engaging end has two tines and the vertical joining member fits between the two tines, thus resulting in three sides each of the two tines being surrounded by the two adjacent spans and the vertical joining member.

2. The revision knee system as claimed in claim 1, wherein the tibial bearing monobloc including the keel is integrally cast as a single unit during manufacture.

3. The revision knee system as claimed in claim 1, wherein the keel occupies less than 60% cross section across the inferior tibial bearing face.

4. The revision knee system as claimed in claim 1, wherein no part of the inferior stem extends above the inferior tibial bearing face.

5. The revision knee system as claimed in 1, wherein the keel is non-circular in cross-section in a transverse plane.

6. The revision knee system as claimed in claim 1, wherein the two adjacent spans widen towards the inferior tibial bearing face.

7. The revision knee system as claimed in claim 1, wherein the two adjacent spans extend mediolaterally.

8. The revision knee system as claimed in claim 1, further comprising fasteners which insert through apertures of the tines and through the vertical joining member.

9. The revision knee system as claimed in claim 1, wherein the superior keel engaging end comprises a backstop tine defining a backstop bearing face configured to bear against a lower edge of the keel.

10. The revision knee system as claimed in claim 9, wherein the backstop bearing face is anteriorly orientated.

11. The revision knee system as claimed in claim 1, further comprising a plurality of augments of differing thicknesses, each configured to engage the inferior tibial bearing face and wherein the augments are conformingly shaped to stack together.

12. The revision knee system as claimed in claim 11, wherein each augment comprises a superior face comprising at least one connector configured for connecting to the inferior tibial bearing face.

13. The revision knee system as claimed in claim 12, wherein each augment comprises an inferior augment bearing face defining an engagement for the at least one connector so as to be able to connect to an adjacent augment in use.

14. The revision knee system as claimed in claim 12, wherein each augment comprises at least one bone cement passage between inferior and superior surfaces thereof.

15. The revision knee system as claimed in claim 14, wherein:
the at least one passage comprises a plurality of passages which are spaced around each augment; and
the passages correspond in location with corresponding cavities in the inferior tibial bearing face such that, in use, bone cement can penetrate into the polymeric tibial bearing monobloc via at least one of the plurality of augments.

16. A revision knee technique using the system as claimed in claim 1, the technique comprising preparing a tibia by preparing at least a tibial cut surface in a transverse plane, selecting the polymeric tibial bearing monobloc by size and connecting the keel thereof with the superior keel engaging end of the inferior stem inferiorly with respect to the inferior tibial bearing face, inserting the inferior stem into the tibial cut surface until the keel penetrates beneath the tibial cut surface to engage into spongy bone thereunderneath and the inferior tibial bearing face of the tibial bearing monobloc bears flush against the tibial cut surface so as to withstand compressive loading force applied to the superior condylar articular bearing surface thereof.

17. The technique as claimed in claim 16, further comprising the system as claimed in claim 15, the technique comprising removing unsuitable bone and selecting at least two augments having a height corresponding to a depth of the removed unsuitable bone, stacking the at least two augments together and connecting the at least two augments to the inferior tibial bearing face of the tibial bearing monobloc.

18. The technique as claimed in claim 17, further comprising the system as claimed in claim 15, further comprising applying bone cement which flows via collocating passages of the augments into cavities within the polymeric tibial bearing monobloc.

19. A revision knee system comprising:
a polymeric tibial bearing monobloc defining a superior condylar articular bearing surface for a femoral component and a planar inferior tibial bearing face opposite the superior condylar articular bearing surface, the tibial bearing monobloc having a keel extending inferiorly from the inferior tibial bearing face; and
an inferior stem comprising an insertion end and a superior keel engaging end, wherein
the superior keel engaging end engages the keel inferiorly with respect to the inferior tibial bearing face along most of the length of the keel,
a portion of the keel forms an exterior of the revision knee system,
the keel extends outwardly from along the superior keel engaging end,
the keel comprises two adjacent spans which extend outwardly from the superior keel engaging end in a transverse plane, the two adjacent spans tightly fit the superior keel engaging end between respective inner surfaces thereof, and
the keel further comprises a vertical joining member between the two adjacent spans, the superior keel engaging end has two tines and the vertical joining member fits between the two tines, thus resulting in three sides each of the two tines being surrounded by the two adjacent spans and the vertical joining member.

* * * * *